(12) United States Patent
Lai et al.

(10) Patent No.: US 12,097,283 B2
(45) Date of Patent: Sep. 24, 2024

(54) METHOD FOR ALLEVIATING DRY EYE SYNDROME

(71) Applicants: Chang Gung University, Taoyuan (TW); Giant Bio Technology Inc., New Taipei (TW)

(72) Inventors: Jui-Yang Lai, Taoyuan (TW); Chih-Ching Huang, Taoyuan (TW); Han-Jia Lin, Taoyuan (TW); Hong-Jyuan Jian, Taoyuan (TW)

(73) Assignees: Chang Gung University, Taoyuan (TW); Giant Bio Technology Inc., New Taipei (TW)

( * ) Notice: Subject to any disclaimer, the term of this patent is extended or adjusted under 35 U.S.C. 154(b) by 55 days.

(21) Appl. No.: 17/933,325

(22) Filed: Sep. 19, 2022

(65) Prior Publication Data

US 2023/0364011 A1 Nov. 16, 2023

(30) Foreign Application Priority Data

May 10, 2022 (TW) .................. 111117498

(51) Int. Cl.
*A61K 9/00* (2006.01)
*A61K 9/08* (2006.01)
*A61K 47/69* (2017.01)
*A61P 27/02* (2006.01)

(52) U.S. Cl.
CPC .............. *A61K 9/0048* (2013.01); *A61K 9/08* (2013.01); *A61K 47/6935* (2017.08); *A61P 27/02* (2018.01)

(58) Field of Classification Search
CPC .......... A61P 27/02; A61K 9/0048; A61K 9/08; A61K 47/6935
See application file for complete search history.

(56) References Cited

U.S. PATENT DOCUMENTS 8,420,699 B1 * 4/2013 Dubow .................. A61K 47/10
514/772.3

OTHER PUBLICATIONS

Pei-Hsuan Lin, et al., Alleviation of Dry Eye Syndrome with One Dose of Antioxidant, Anti-inflammatory, and Mucoadhesive Lysine-Carbonized Nanogels, 141 Acta Biomat. 140 (Year: 2022).*
Peili Li, et al., Carbon Quantum Dots Derived from Lysine and Arginine Simultaneously Scavenge Bacteria and Promote Tissue Repair, 19 Appl. Mat. Today 100601 (Year: 2020).*
D. Chou et al., "Carbonized Lysine-Nanogels Protect against Infectious Bronchitis Virus," Int. J. Mol. Sci., 22, pp. 1-10, 2021, https://doi.org/10.3390/ijms22115415 (10 pages).
J. Mao et al., "Carbon nanogels exert multipronged attack on resistant bacteria and strongly constrain resistance evolution," J. Colloid Interface Sci., 608, pp. 1813-1826, 2022, https://doi.org/10.1016/j.jcis.2021.10.107) (14 pages).

* cited by examiner

*Primary Examiner* — Sean M Basquill
(74) *Attorney, Agent, or Firm* — Osha Bergman Watanabe & Burton LLP

(57) ABSTRACT

Disclosed herein is a method for alleviating dry eye syndrome using a composition containing a polylysine nanoparticle. The polylysine nanoparticle is produced by subjecting lysine hydrochloride to a pyrolysis treatment at a temperature ranging from 240° C. to 280° C.

5 Claims, 5 Drawing Sheets

METHOD FOR ALLEVIATING DRY EYE SYNDROME

CROSS-REFERENCE TO RELATED APPLICATION

This application claims priority of Taiwanese Invention Patent Application No. 111117498, filed on May 10, 2022.

FIELD

The present disclosure relates to a method for alleviating dry eye syndrome using a composition containing a polylysine nanoparticle.

BACKGROUND

Dry eye syndrome (DES) (also known as keratoconjunctivitis sicca (KCS) or dysfunctional tear syndrome (DTS)) is a multifactorial disease of tear and ocular surface. The main causes of DES are insufficient tear production and excessive tear evaporation. DES might cause dryness, redness, itching, pain, and eventually, visual disturbance and ocular surface damage.

The current clinical treatment strategies for DES include use of artificial tears to relieve the symptoms of dryness, and use of cyclosporine, non-steroidal anti-inflammatory drugs (NSAIDs), or steroidal anti-inflammatory drugs (SAIDs) to reduce inflammation. However, these treatment strategies might not be able to achieve the desired therapeutic effect and might also cause severe side effects and adverse effects. For example, cyclosporine A (CsA) ophthalmic emulsion (Restasis®) must be administered twice daily for a sufficiently long period to achieve significant therapeutic effect. In addition, CsA ophthalmic emulsion might cause side effects, such as eye burning, eye irritation, conjunctival congestion, increased eye discharge, and blurred vision.

Polylysine nanoparticles (also known as carbonized nanogels, CNGs) are formed by subjecting lysine hydrochloride (lysine HCl) to a pyrolysis treatment (i.e., a carbonization process). Polylysine nanoparticles have embedded crystalline graphene-like structures, and have been demonstrated to have antiviral and antibacterial activities (Chou D. L. et al. (2021), Int. J. Mol. Sci., doi: 10.3390/ijms22115415; Mao J. Y. et al. (2022), J. Colloid Interface Sci., doi: 10.1016/j.jcis.2021.10.107).

In spite of the aforesaid, there is still a need to develop an effective way for alleviating DES.

SUMMARY

Accordingly, the present disclosure provides a method for alleviating dry eye syndrome, which can alleviate at least one of the drawbacks of the prior art, and which includes administering to a subject in need thereof a composition containing a polylysine nanoparticle.

The polylysine nanoparticle is produced by subjecting lysine hydrochloride to a pyrolysis treatment at a temperature ranging from 240° C. to 280° C.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
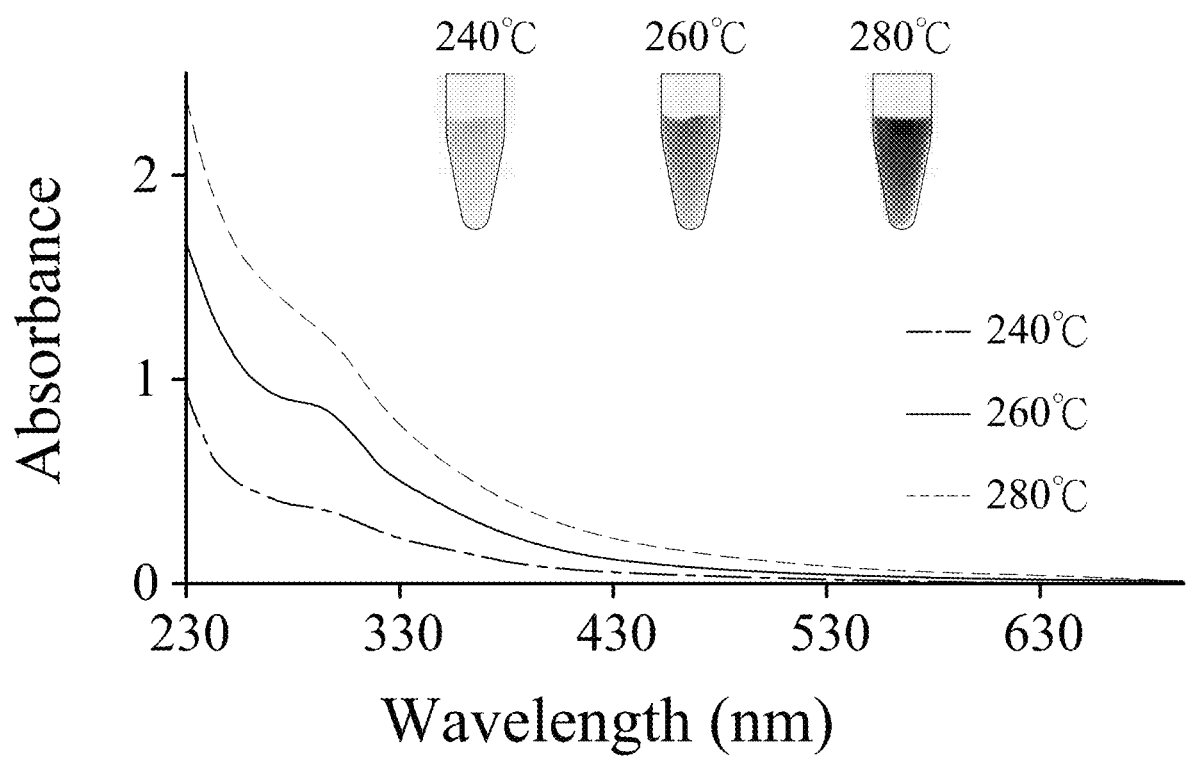
FIG. 1 shows the UV-visible absorption spectra of dialysates prepared at different pyrolysis temperatures.

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The present disclosure provides a method for alleviating dry eye syndrome, which includes administering to a subject in need thereof a composition containing a polylysine nanoparticle.

The polylysine nanoparticle is produced by subjecting lysine hydrochloride (lysine HCl) to a pyrolysis treatment at a temperature ranging from 240° C. to 280° C.

As used herein, the term "alleviating" or "alleviation" refers to at least partially reducing, ameliorating, relieving, controlling, treating or eliminating one or more clinical signs of a disease or disorder; and lowering, delaying, stopping or reversing the progression of severity regarding the condition or symptom being treated and preventing or decreasing the likelihood or probability thereof.

As used herein, the term "administering" or "administration" means introducing, providing or delivering the above-mentioned composition to a subject showing condition(s) or symptom(s) of a disorder by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

As used herein, the term "dry eye syndrome" can be used interchangeably with other terms such as "xerophthalmia", "keratoconjunctivitis sicca", and "dysfunctional tear syndrome".

It should be noted that the operating conditions of the pyrolysis treatment may vary, depending on the peripheral instruments and equipment used, the proportion of the amounts of lysine HCl used, etc. The actual operating conditions necessary for the pyrolysis treatment are well known in the art, and may be adjusted according to practical requirements. In this regard, those skilled in the art may refer to journal articles, e.g., Chou D. L. et al. (2021), supra.

In certain embodiments, the pyrolysis treatment may be conducted for a time period ranging from 2 hours to 5 hours. In an exemplary embodiment, the pyrolysis treatment is conducted at 260° C. for 3 hours.

In certain embodiments, after the pyrolysis treatment, the unreacted lysine HCl may be removed using standard techniques well known to those skilled in the art. In an exemplary embodiment, the unreacted lysine HCl is removed by conducting a dialysis treatment.

In certain embodiments, the polylysine nanoparticle may have a particle size ranging from 200 nm to 1000 nm. In an exemplary embodiment, the polylysine nanoparticle has a particle size ranging from 200 nm to 700 nm.

In certain embodiments, the polylysine nanoparticle may have a d-spacing value ranging from 0.23 nm to 0.36 nm. In an exemplary embodiment, the polylysine nanoparticle has a d-spacing value ranging from 0.26 nm to 0.33 nm.

In certain embodiments, the polylysine nanoparticle may have a zeta potential value ranging from 11.4 mV to 37.3 mV. In an exemplary embodiment, the polylysine nanoparticle has a zeta potential value ranging from 15 mV to 30 mV.

In certain embodiments, the polylysine nanoparticle may have a covalent bond selected from the group consisting of C—N, C=C, C=O, and combinations thereof.

According to the present disclosure, the dry eye syndrome may be selected from the group consisting of aqueous tear-deficient dry eye syndrome, mucin-deficient dry eye syndrome, lipid-deficient dry eye syndrome (also known as evaporative dry eye syndrome), abnormal tear dynamics dry eye syndrome, and combinations thereof.

According to the present disclosure, the dry eye syndrome may be caused by one or more of the following factors: deficiency in the structure of the eyelid, deficiency in the tear-flow system of the eye, natural aging process (particularly menopause), medications (such as antihistamines and blood pressure drugs), and diseases which affect the ability to produce tears (such as Sjogren's syndrome, rheumatoid arthritis, and vitamin A deficiency).

According to the present disclosure, the composition may be prepared in the form of a pharmaceutical composition. The pharmaceutical composition may be formulated into a dosage form suitable for topical ophthalmic administration using technology well known to those skilled in the art.

According to the present disclosure, the dosage form suitable for topical ophthalmic administration includes, but is not limited to, drops, emulsions, gels, ointments, creams, sprays, suspensions, and the like.

According to the present disclosure, the pharmaceutical composition may further include a pharmaceutically acceptable carrier widely employed in the art of drug-manufacturing. For instance, the pharmaceutically acceptable carrier may include one or more of the following agents: solvents (such as sterile water), buffers (such as ophthalmic balanced salt solutions, phosphate buffered saline (PBS), Ringer's solution, and Hank's solution), emulsifiers, suspending agents, decomposers, pH adjusting agents, stabilizing agents, chelating agents, diluents, preservatives, absorption delaying agents, liposomes, and the like. The choice and amount of the aforesaid agents are within the expertise and routine skills of those skilled in the art.

The dose and frequency of administration of the pharmaceutical composition may vary depending on the following factors: the severity of the illness or disorder to be treated, routes of administration, and age, physical condition and response of the subject to be treated. In general, the pharmaceutical composition may be administered in a single dose or in several doses.

The disclosure will be further described by way of the following examples. However, it should be understood that the following examples are solely intended for the purpose of illustration and should not be construed as limiting the disclosure in practice.

EXAMPLES

General Experimental Materials

1. Lysine hydrochloride (lysine HCl) (Cat. No. L4605) used in the following experiments was purchased from Sigma-Aldrich.
2. Cyclosporine A (CsA) ophthalmic emulsion (Restasis®) used in the following experiments was purchased from Allergan Pharmaceuticals Taiwan Co., Ltd.

General Procedures

1. Statistical Analysis

All the experiments described below were performed in triplicates. The experimental data of all the test groups are expressed as mean±standard deviation (SD), and were analyzed using one-way analysis of variance (ANOVA) followed by Student's t-test, so as to evaluate the differences between the groups. Statistical significance is indicated by $p<0.05$.

Example 1. Preparation of Polylysine Nanoparticle

A. Pyrolysis of Lysine HCl at Different Temperatures 300 mg of lysine HCl was mixed with 1 mL of deionized water, and the resultant mixture was subjected to a pyrolysis treatment (also known as carbonization) at a designated temperature (240° C., 260° C., or 280° C.) for 3 hours. The pyrolyzed product thus obtained was allowed to cool to room temperature, followed by adding 10 mL of deionized water. The resultant mixture was subjected to a sonication treatment for 1 hour. Subsequently, centrifugation at 5,000 g was performed for 30 minutes, and the resultant supernatant was collected, followed by conducting dialysis using a dialysis membrane with a molecular weight cut-off value of 1 kDa and deionized water for 5 hours, so as to obtain a dialysate which was a brown liquid containing polylysine nanoparticles.

The dialysate was diluted 10-fold by deionized water, and then subjected to light absorbance measurement using a monochromatic microplate spectrophotometer (Synergy 4 Multi-Mode, Biotek Instruments, Winooski, VT, USA), so as to obtain a UV-visible absorption spectrum.

FIG. 1 shows the UV-visible absorption spectra of the dialysates prepared at different pyrolysis temperatures. As shown in FIG. 1, the dialysate obtained at a pyrolysis temperature of 240° C., 260° C., or 280° C. had a maximum absorbance at a wavelength of 300 nm, indicating that a $\pi \rightarrow \pi^*$ (pi to pi*) conversion occurred, resulting in the formation of graphene-like nanostructures which contain C=C bonds.

These results indicate that pyrolysis of lysine HCl at a respective one of 240° C., 260° C., and 280° C. can successfully generate polylysine nanoparticles, which are represented by PLNP1, PLNP2, and PLNP3, respectively.

B. Morphological Analysis

Morphological analysis of PLNP1, PLNP2, and PLNP3 obtained in section A of this example was performed using a Tecnai 20 G2 S-Twin transmission electron microscope (Philips/FEI, Hillsboro, OR, USA). The results are shown in Table 1 below. These results indicate that the respective one of PLNP1, PLNP2, and PLNP3 has an embedded crystalline graphene-like structure.

TABLE 1

| Polylysine nanoparticle | Particle size (nm) | D-spacing value (nm) |
|---|---|---|
| PLNP1 | 1,000 | 0.26 |
| PLNP2 | 600 | 0.33 |
| PLNP3 | 200 | 0.33 |

C. Fourier Transform Infrared Spectroscopy (FTIR) Analysis

A suitable amount of a respective one of PLNP1, PLNP2, and PLNP3 obtained in section A of this example and lysine HCl was freeze-dried, and the respective resultant freeze-dried powder was mixed with potassium bromide in a ratio of 1:99 (w/w), followed by compressing into a tablet. Each tablet was subjected to FTIR analysis using an Agilent Cary 640 FT-IR spectrometer (Santa Clara, CA, USA).

Figure 2:
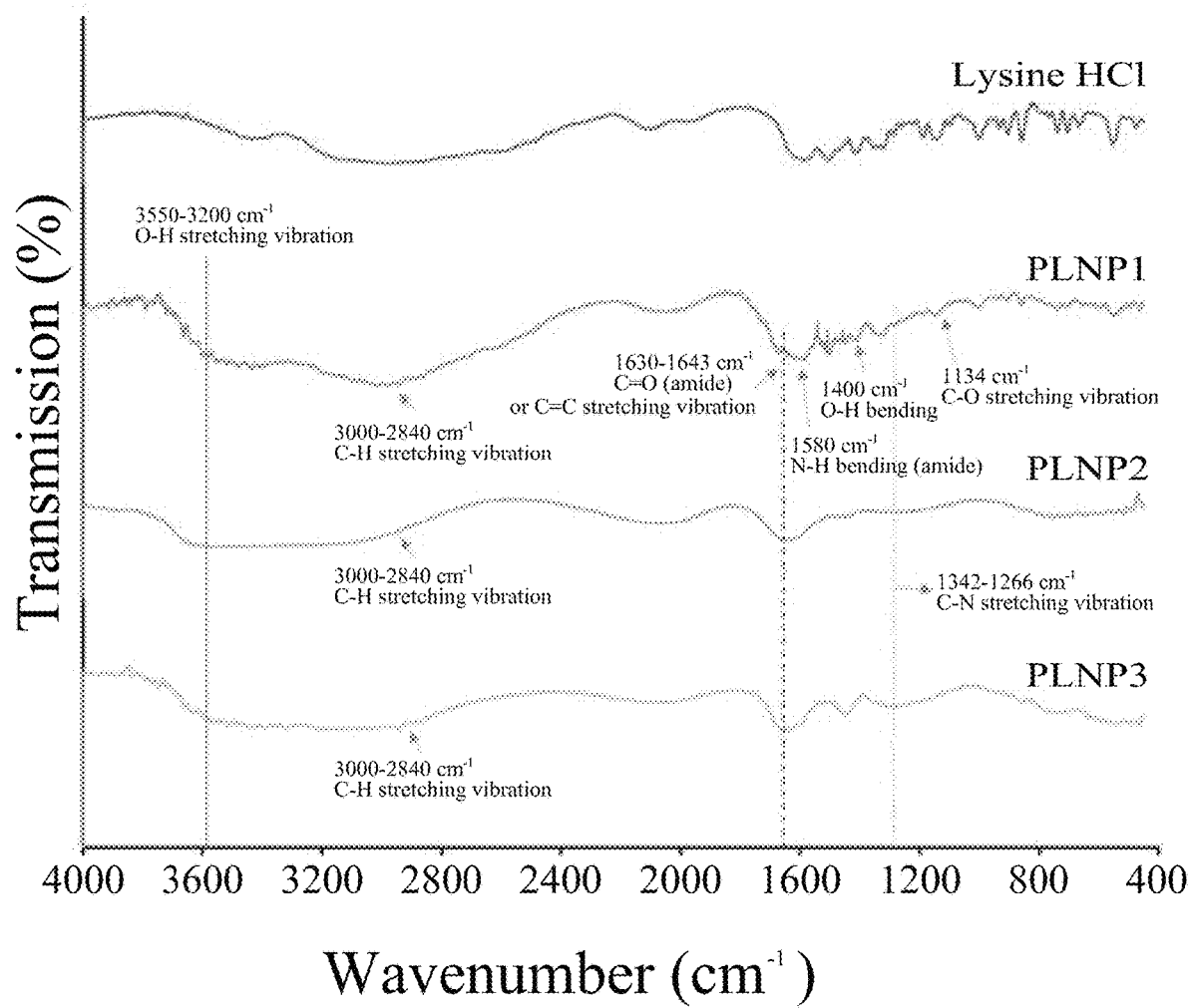
FIG. 2 shows the Fourier transform infrared spectroscopy (FTIR) spectra of polylysine nanoparticle 1 (PLNP1), polylysine nanoparticle 2 (PLNP2), and polylysine nanoparticle 3 (PLNP3)

Referring to FIG. 2, the FTIR spectrum of the respective one of PLNP1, PLNP2, and PLNP3 was different from that of lysine HCl. In particular, the respective one of PLNP1, PLNP2, and PLNP3 had several absorption bands at 1342-1266 $cm^{-1}$ (C—N stretching vibration), 1630 $cm^{-1}$ (C=C stretching vibration), and 1643 $cm^{-1}$ (C=O stretching vibration).

These results indicate that the bonding and structural properties of PLNP1, PLNP2, and PLNP3 are different from those of lysine HCl.

D. Zeta Potential Analysis

A suitable amount of a respective one of PLNP1, PLNP2, and PLNP3 obtained in section A of this example was dissolved in a 5 mM phosphate buffer (pH 7.4). The respective resultant mixture was subjected to zeta potential analysis using a Zetasizer Nano ZS analyzer (Nano ZS, Malvern Instruments, Worcestershire, UK). The results show that the zeta potential values of PLNP1, PLNP2, and PLNP3 are 11.4 mV, 22.8 mV, and 37.3 mV, respectively.

Example 2. Evaluation for the Effect of Polylysine Nanoparticle on Alleviating Dry Eye Syndrome (DES)

A. Test Animals

New Zealand white rabbits (16-20 weeks old, a body weight of 3-3.5 kg) were purchased from National Laboratory Animal Breeding and Research Center, Taipei, Taiwan. The rabbits were kept in an animal room with an independent air conditioning system under the following laboratory conditions: a 12 hour light/12 hour dark cycle, a temperature of 20-24° C., and a relative humidity of 55-65%. Furthermore, water and feed were provided ad libitum for all the experimental animals. All animal testing procedures were approved by the Institutional Animal Care and Use Committee (IACUC) of Chang Gung University, and were carried out in accordance with the ARVO Statement for the Use of Animals in Ophthalmic and Vision Research.

B. Preparation of Ophthalmic Solution Containing PLNP2

A suitable amount of PLNP2 obtained in section A of Example 1 was dissolved in 0.1 mL of phosphate-buffered saline (PBS), so as to obtain an ophthalmic solution containing 50 μg/mL of PLNP2.

C. Induction of Dry Eye Syndrome (DES)

The New Zealand white rabbits were divided into seven groups, including a normal control group (NCG), a pathological control group (PCG), two comparative groups (i.e., comparative group 1 (CG1) and comparative group 2 (CG2)), and three experimental groups (i.e., experimental group 1 (EG1), experimental group 2 (EG2), and experimental group 3 (EG3)) (n=6 per group). 50 μL of a 0.15% benzalkonium chloride (BAC) solution was topically instilled into the ocular surface of the respective rabbit of the PCG, CG1, CG2, EG1, EG2, and EG3. Each rabbit was administered twice daily for a total period of 14 days, so as to induce DES. In addition, the rabbits of the NCG received no treatment.

D. Administration of Ophthalmic Solution Containing PLNP2

After completion of the induction of DES at the end of the $14^{th}$ day as described in section C of this example, 50 μL of the ophthalmic solution prepared in section B of this example was topically instilled into the ocular surface of the respective rabbit of the EG1, EG2, and EG3, while 50 μL of the CsA ophthalmic emulsion described in section 2 of "General Experimental Materials" was topically instilled into the ocular surface of the respective rabbit of the CG1 and CG2. Each rabbit was administered for a 4-day treatment period. In addition, the rabbits of the NCG and PCG received no treatment.

The treating agent, and the dose and frequency of administration thereof for each group are summarized in Table 2 below.

TABLE 2

| | Treating agent | | |
|---|---|---|---|
| Group | Ophthalmic solution of the present disclosure (μg/mL) | CsA ophthalmic emulsion (μg/mL) | Frequency of administration |
| NCG | — | — | — |
| PCG | — | — | — |
| CG1 | — | 500 | Twice daily |
| CG2 | — | 50 | Twice daily |
| EG1 | 50 | — | Twice daily |
| EG2 | 50 | — | Once every 2 days |
| EG3 | 50 | — | Once every 4 days |

E. Morphological Observation

Prior to the administration of the treating agent as described in section D of this example (i.e., at the $0^{th}$ day) and at the end of a respective one of the $1^{st}$, $2^{nd}$, $3^{rd}$, and $4^{th}$ days after starting the administration of the treating agent, the change in the ocular surface of each rabbit was analyzed using a method slightly modified from that described by Tsubota K. et al. (2000), *Invest. Ophthalmol. Vis. Sci.*, 41:1666-1673. Briefly, 2 μL of a 1% fluorescein sodium solution was topically instilled into the ocular surface of each rabbit. Next, the corneal epithelial morphology of the rabbit eye was observed by slit-lamp biomicroscopy (Topcon Optical, Tokyo, Japan) using cobalt blue illumination, and the corneal epithelial injury was assessed visually by scoring on a scale ranging from 0 to 9 (the higher the scale, the more serious the ocular symptom was).

The data thus obtained were analyzed according to the method described in section 1 of "General Procedures".

Figure 3:
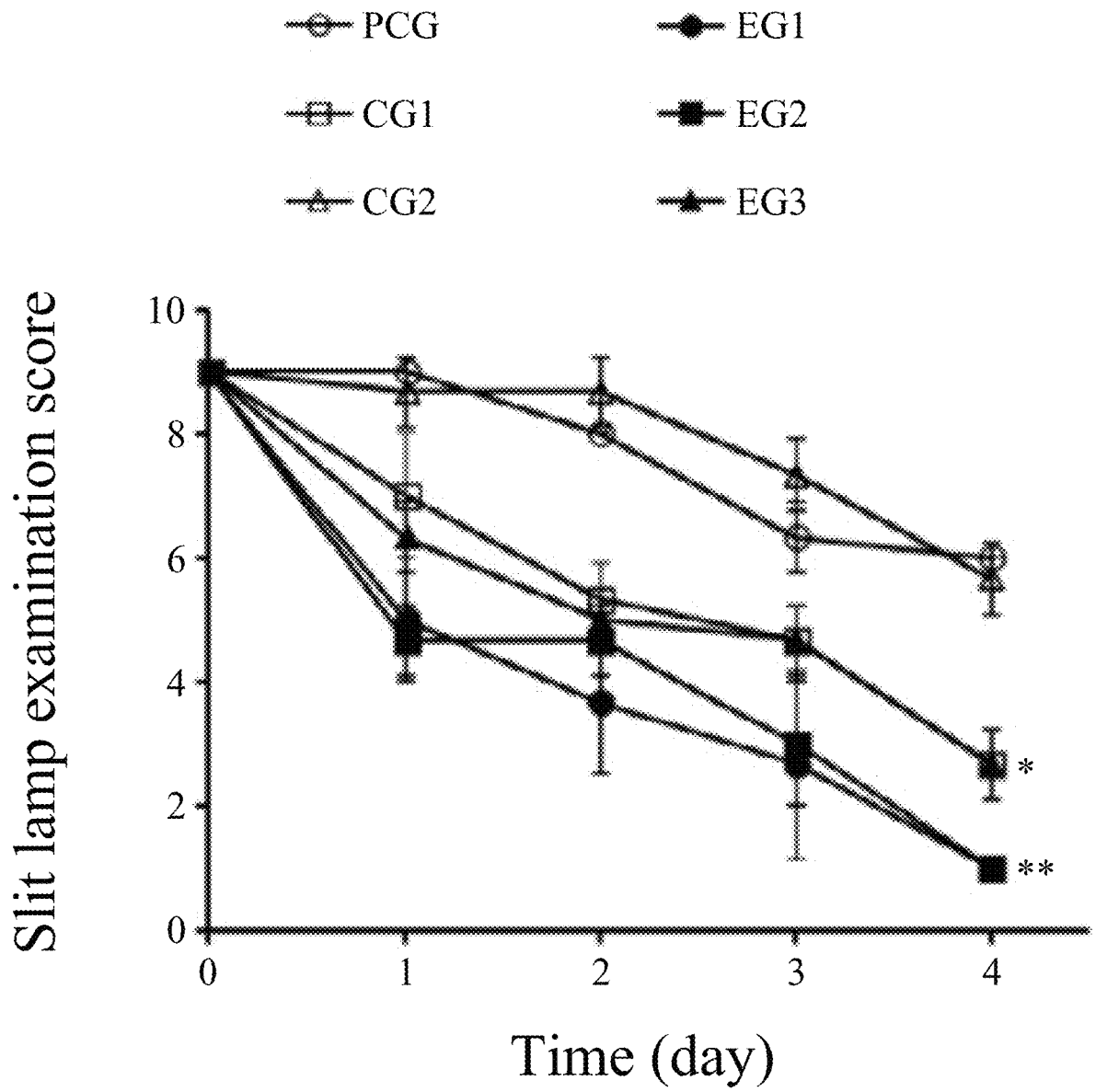
FIG. 3 shows the slit lamp examination scores determined in the PCG, EG1 to EG3, and CG1 to CG2 of Example 2, infra, in which the symbols "*" and "**" respectively represent $p<0.001$ and $p<0.00001$ (compared with the PCG)

Referring to FIG. 3, the slit lamp examination scores determined in the EG1 to EG3 and CG1 were each significantly lower than that determined in the PCG. It should be noted that, the slit lamp examination score determined in the EG3 was similar to that of the CG1, while no significant difference was observed on the slit lamp examination score among the CG2 and PCG.

These results indicate that the CsA ophthalmic emulsion must be administered twice daily at a dose of 500 μg/mL to alleviate corneal epithelial injury. On the contrary, the ophthalmic solution of the present disclosure only require a dose of 50 μg/mL once every 4 days to effectively alleviate corneal epithelial injury.

F. Schirmer Tear Test (STT)

At the end of the $4^{th}$ day after starting the administration of the treating agent as described in section D of this example, a Schirmer tear test strip (Color Bar Schirmer Tear Test, Eagle Vision Inc., Memphis, TN, USA) was placed into the lower eyelid of the respective rabbit of the EG1 to EG3, PCG, and CG1 for 5 minutes. Thereafter, the Schirmer tear test strip was taken out from each rabbit, and the wetted length was measured.

The data thus obtained were analyzed according to the method described in section 1 of "General Procedures".

As shown in Table 3 below, the wetted length determined in each of the PCG and CG1 was significantly lower than the normal value (i.e., 12 mm), while the wetted length determined in each of the EG1, EG2, and EG3 was higher than the normal value. These results demonstrate that the ophthalmic solution of the present disclosure can effectively alleviate abnormal preocular tear film and insufficient tear production caused by dry eye syndrome.

TABLE 3

| Group | Wetted length (mm) |
|---|---|
| PCG | 8.2 ± 0.8 |
| CG1 | 9.1 ± 0.9 |
| EG1 | 15.6 ± 1.1 |
| EG2 | 15.4 ± 1.3 |
| EG3 | 12.1 ± 0.8 |

G. Conjunctival Impression Cytology (CIC) Analysis

After completion of the tests at the end of the $4^{th}$ day as described in sections E and F of this example, the respective rabbit of the EG1 to EG3, PCG, NCG, and CG1 was anesthetized via subcutaneous injection of a mixture of Zoteil and Rompun (1:1, v/v), followed by placing a nitrocellulose filter paper on the surface of the nasal and bulbar conjunctiva, so as to obtain a conjunctival impression cytology (CIC) sample. Next, the respective rabbit was sacrificed, and the corneal tissue was obtained from the respective rabbit carcass.

The CIC sample was subjected to a fixation treatment with a formalin-ethanol solution at room temperature for 1 minute, and then was washed with distilled water, followed by conducting periodic acid-Schiff (PAS) staining using PAS kit (Sigma-Aldrich, Cat. No. 395B) in accordance with the manufacturer's instructions. The resultant stained CIC sample was observed under an optical microscope (Carl Zeiss, Oberkochen, Germany) at a magnification of 400×. Three areas of the respective stained CIC sample were randomly selected and photographed, and the number of goblet cells in the respective stained CIC sample was counted.

The data thus obtained were analyzed according to the method described in section 1 of "General Procedures".

Figure 4:
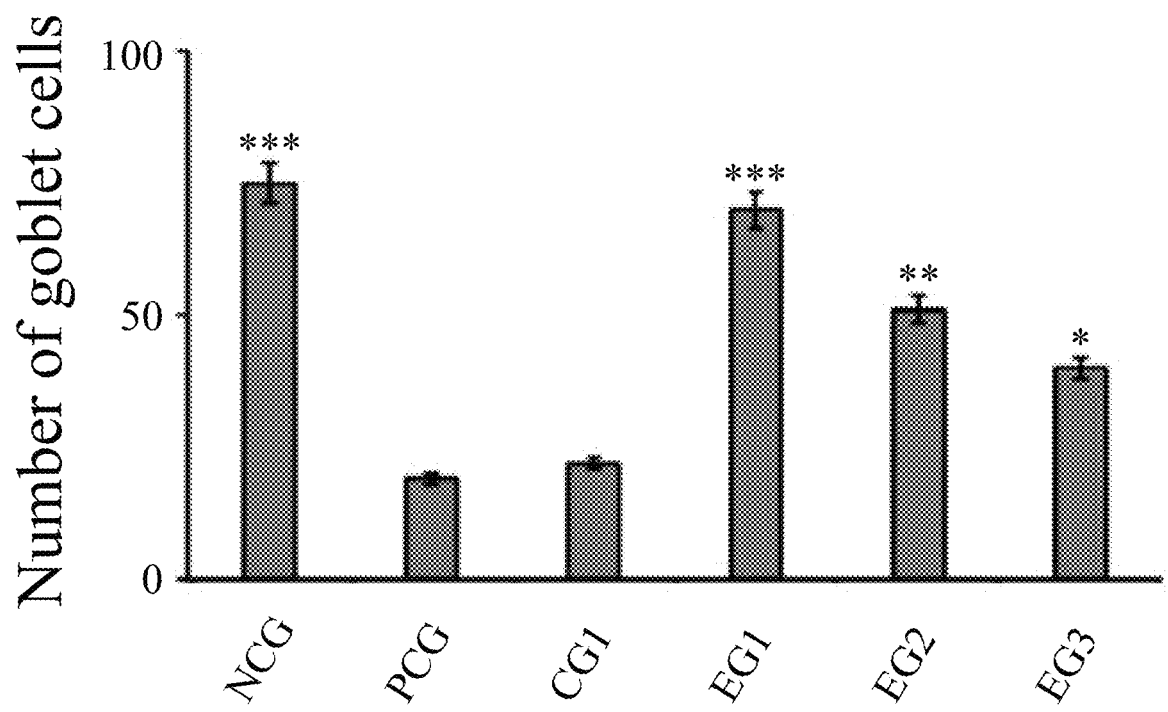
FIG. 4 shows the numbers of goblet cells determined in the NCG, PCG, EG1 to EG3, and CG1 of Example 2, infra, in which the symbols "*", "", and "*" respectively represent $p<0.05$, $p<0.005$, and $p<0.001$ (compared with the PCG)

Referring to FIG. 4, the numbers of goblet cells determined in the EG1 to EG3 and NCG were each significantly higher than those determined in the PCG and CG1. It should be noted that no significant difference was observed on the number of goblet cells among the CG1 and PCG. These results indicate that the ophthalmic solution of the present disclosure can effectively alleviate goblet cell loss caused by dry eye syndrome.

H. Histopathologic Analysis 0.02 g of the corneal tissue of each rabbit obtained in section G of this example was subjected to a fixation treatment with a 4% paraformaldehyde solution (in PBS) at room temperature for 2 hours. The fixed tissue sample was then embedded with paraffin, followed by slicing to obtain a tissue section having a thickness of 5 μm.

The tissue section was subjected to hematoxylin-eosin staining using a staining protocol well-known to those skilled in the art, and then was observed under an optical microscope (Carl Zeiss, Oberkochen, Germany) at a magnification of 10×. One area of the respective tissue section was randomly selected and photographed, and the corneal epithelial thickness in the respective tissue section was determined.

The data thus obtained were analyzed according to the method described in section 1 of "General Procedures".

Figure 5:
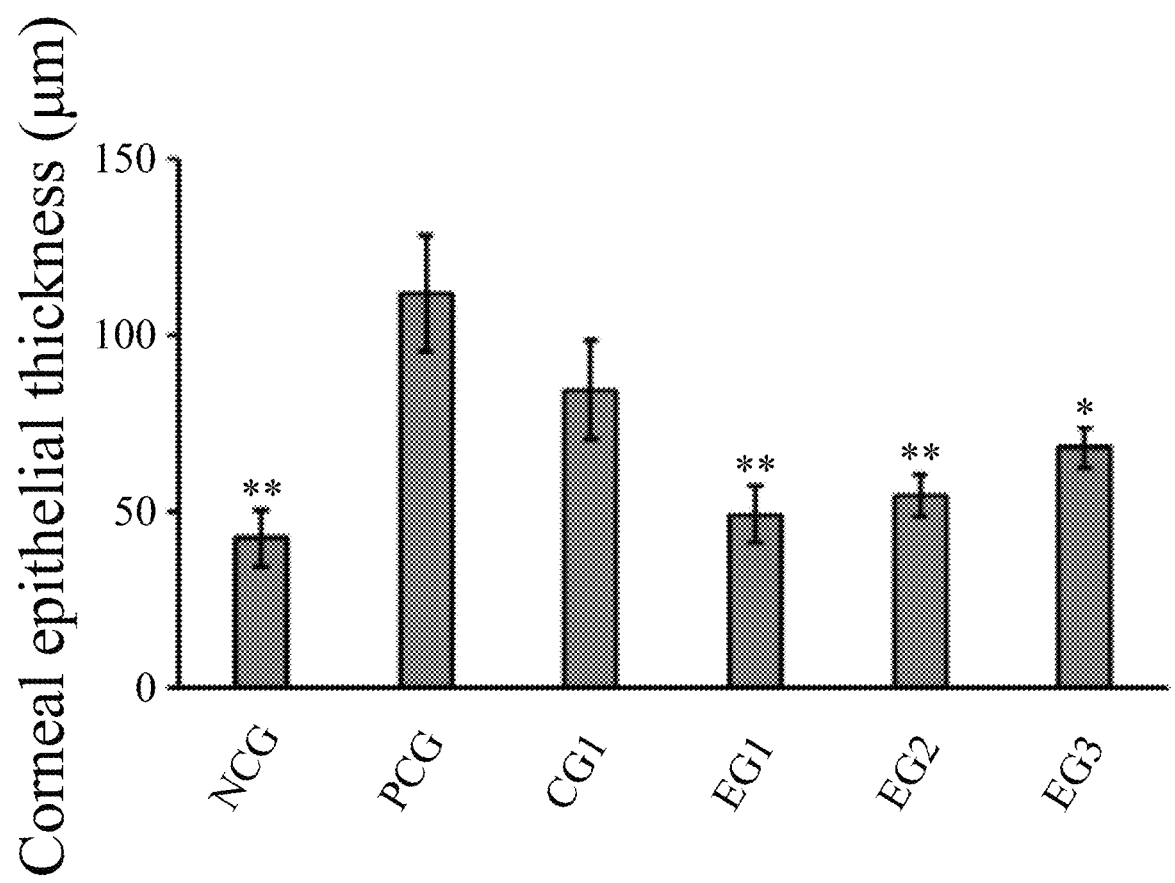
FIG. 5 shows the corneal epithelial thicknesses determined in the NCG, PCG, EG1 to EG3, and CG1 of Example 2, infra, in which the symbols "*" and "**" respectively represent $p<0.05$ and $p<0.005$ (compared with the PCG).

Referring to FIG. 5, the corneal epithelial thicknesses determined in the EG1 to EG3 and NCG were each significantly lower than those determined in the PCG and CG1. It should be noted that no significant difference was observed on the corneal epithelial thickness among the CG1 and PCG. These results indicate that the ophthalmic solution of the present disclosure can effectively alleviate abnormal corneal thickening caused by dry eye syndrome.

Summarizing the above test results, it is clear that the polylysine nanoparticle of the present disclosure can effectively ameliorate various pathological signs caused by dry eye syndrome, and hence is expected to be useful for treating and/or alleviating dry eye syndrome.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for alleviating dry eye syndrome, comprising administering to a subject in need thereof a composition containing a polylysine nanoparticle, the polylysine nanoparticle being produced by the step of:
    subjecting lysine hydrochloride to a pyrolysis treatment at a temperature ranging from 240° C. to 280° C.

2. The method as claimed in claim 1, wherein the polylysine nanoparticle has a particle size ranging from 200 nm to 1000 nm.

3. The method as claimed in claim 1, wherein the polylysine nanoparticle has a zeta potential value ranging from 11.4 mV to 37.3 mV.

4. The method as claimed in claim 1, wherein the composition is formulated as a pharmaceutical composition.

5. The method as claimed in claim 4, wherein the pharmaceutical composition is in a dosage form for topical ophthalmic administration.

\* \* \* \* \*